United States Patent
Bosetto et al.

[11] Patent Number: 5,938,938
[45] Date of Patent: Aug. 17, 1999

[54] AUTOMATIC DIALYSIS METHOD AND APPARATUS

[75] Inventors: Antonio Bosetto, Mirandola; Francesco Paolini, Modena, both of Italy

[73] Assignee: Hospal AG, Basel, Switzerland

[21] Appl. No.: 08/836,758

[22] PCT Filed: Jul. 3, 1996

[86] PCT No.: PCT/IB96/00644

§ 371 Date: May 21, 1997

§ 102(e) Date: May 21, 1997

[87] PCT Pub. No.: WO97/02057

PCT Pub. Date: Jan. 23, 1997

[30] Foreign Application Priority Data

Jul. 4, 1995 [IT] Italy ................... TO95A0560

[51] Int. Cl.$^6$ ............. A61M 1/16; G05B 13/04; B01D 61/32

[52] U.S. Cl. .............. 210/739; 210/85; 210/86; 210/97; 210/102; 210/134; 210/138; 210/143; 210/645; 210/646; 210/647; 210/744; 364/148; 364/149; 364/150; 364/151; 364/188

[58] Field of Search ............. 210/645, 646, 210/647, 739, 744, 85, 86, 97, 102, 134, 138, 143, 929; 364/148, 149, 150, 151, 188

[56] References Cited

U.S. PATENT DOCUMENTS

| | | | |
|---|---|---|---|
| 4,324,663 | 4/1982 | Hirel et al. | 210/646 |
| 4,923,613 | 5/1990 | Chevallet | 210/647 |
| 5,346,472 | 9/1994 | Keshaviah et al. | 605/4 |
| 5,609,770 | 3/1997 | Zimmerman et al. | 210/739 |
| 5,620,608 | 4/1997 | Rosa et al. | 210/739 |

FOREIGN PATENT DOCUMENTS

| | | |
|---|---|---|
| 0 029 793 | 6/1981 | European Pat. Off. |
| 0 089 003 | 9/1983 | European Pat. Off. |
| 0 186 973 A2 | 7/1986 | European Pat. Off. |
| 0 186 973 A3 | 7/1986 | European Pat. Off. |
| 0 291 421 A1 | 11/1988 | European Pat. Off. |
| 0 547 210 | 6/1993 | European Pat. Off. |
| 27 34 075 A1 | 2/1978 | Germany. |
| 2 052 303 | 1/1981 | United Kingdom. |
| WO93/00938 | 1/1993 | WIPO. |

*Primary Examiner*—John Kim
*Attorney, Agent, or Firm*—Finnegan, Henderson, Farabow, Garrett & Dunner, L.L.P.

[57] ABSTRACT

A method for automatic dialysis using a dialysis unit which, in service, is connected to a patient undergoing a dialysis treatment, including the phases of acquiring allowed values of input parameters and desired values of patient parameters, acquiring actual values of the patient parameters, the patient parameters including the relative variation in blood volume (BV) and the weight loss (WL), acquiring actual values of machine parameters including the weight loss rate (WLR) and the conductivity of the (CD) dialysis fluid, and controlling the operation of the dialysis unit using controlled values of the machine parameters to make the patient parameters take on the desired values.

21 Claims, 6 Drawing Sheets

AUTOMATIC DIALYSIS METHOD AND APPARATUS

BACKGROUND OF THE INVENTION

1. Field of the Invention

The present invention relates to an automatic dialysis method and apparatus.

2. Description of the Related Art

As is known in the case of patients undergoing a conventional haemodialysis treatment, collateral effects are often found to occur, which are characterized by slight hypotension phenomena or even by collapse phenomena.

These phenomena are caused by the fact that, for their operation, current dialysis apparatuses provide for the establishment of a set of predefined values and act on the patient in open loop, using no feedback information originating from the patient himself. In a significant percentage of cases, this leads to having clinical complications caused by the extreme variability in the capacity of the patient to withstand a given loss of weight.

In order to avoid these undesirable drawbacks, it is suitable to monitor certain patient parameters which indicate his state of health.

Previous inventions, for example, relate to apparatuses based on controlling the patient's blood volume, measured as the relative variation in the blood volume (BV) circulating in the body with respect to the start of the session, and control systems which can make the BV follow a predefined profile, with the aim of solving the problem of hypovolaemia which often occurs spontaneously. The percentage variation in the blood volume circulating in the body can be measured using several methods, for example the one described in patent TO91A000527 in the name of the Applicant Company, which, as a quantity indicating the patient's well-being, takes into consideration the cystolic blood pressure whose correlation with the BV is known.

Conversely, other inventions relate to apparatuses which control particular patient parameters, as stated, for example, in patent applications EP-A-029 793 and EP-A-089 003. In particular, patent EP-A-029 793 in the name of Thomasset describes a system comprising measurement of the impedance of the blood and an apparatus which injects sodium chloride into the patient when the measured impedance value departs from predefined thresholds. This system produces simple feedback of the stop/go type which is scarcely efficient from the clinical point of view.

In contrast, patent EP-A-089 003 in the name of TOYOTA CHUO KENKYUSHO describes an apparatus based on an elementary control system aiming to make the blood volume follow a profile which is fixed beforehand at the start of the treatment, on the basis of the condition of the patient. In this known system, the haematocrit is measured in order to obtain the variations in the blood volume. However, it is demonstrated that measuring the haematocrit is not sufficient for determining the variations in the blood volume, in so far as the assumption forming the basis of the one-to-one relationship between the haematocrit and the variation in the blood volume, that is to say the assumption of constant total cell volume, is rarely satisfied. In any case, the proposed type of control is not suitable for application to an entire population of patients or to different sessions for a single patient, or even to different times during the same session, since it does not take into account the individual reactions to the treatment, which not only are generally different from one patient to another but may also vary for the same individual at different times. Furthermore, the limitations to which the machine parameter manipulation is subject are not taken into account in this patent. This is why the described system is ineffective if there are significant variations in the patient's intradialysis behaviour pattern.

An aspect which has not yet been resolved in any existing dialysis system is the full harmonization of different clinical objectives, to obtain which it is constantly necessary to make compromises between expediently obtaining a result, for example the final weight loss (TWL) which contributes to maintaining the patient's conditions of well-being in the medium and long term, and the final reduction in the blood volume (TVB) which allows intradialysis haemodynamic stabilization with, a consequent reduction in pathology during treatment. In traditional dialysis, the clinical evaluation relating to this compromise is made approximately by the doctor who, for each individual dialysis, chooses the treatment parameters which he adopts, on the basis of his own experience after having determined their effects on the patient, for example the weight loss rate (WLR) defined as the difference between the ultrafiltration rate (UFR) and the transfusion rate ($Q_{inf}$), the conductivity of the dialysis fluid (CD), and may possibly have to review his choice during the treatment subsequent to collapse phenomena.

However, in the automatic dialysis system which is mentioned, this compromise must still be made by hand during the phase of prescribing the treatment, and the situation must be reviewed during the treatment in accordance with the impossibility of simultaneously obtaining the relevant point objectives. This discontinuous management of the dialysis treatment has the effect of partially offsetting the advantages obtained by the automatic system. This is because performing automatic dialysis using the methods mentioned requires great experience in formulating the prescription in the form of desired profiles, and quick intervention if the prescription is inappropriate or cannot be continued because of the patient's contingent conditions.

SUMMARY OF THE INVENTION

The object of the present invention is therefore to provide an automatic dialysis method and apparatus which are free from the drawbacks described above, and which therefore allow the doctor's prescription to be formulated both in terms of WL and in terms of BV, while furthermore defining the relative importance of obtaining each of the two final objectives, considered individually, by means of tolerance limits allocated to each of them.

In particular, the intention is to provide a method and an apparatus capable of producing a final patient condition between the intended limits of the clinical prescription which, at the start of the treatment, makes it possible to define time-varying value intervals between which the controlled parameters BV and WL should lie at each moment during the treatment.

According to the invention, an automatic dialysis method and apparatus as they are defined by claims 1 and 12 are provided.

BRIEF DESCRIPTION OF THE DRAWINGS

For better understanding of the invention, a preferred embodiment will now be described by way of non-limiting example, with reference to the appended drawings, in which.

DETAILED DESCRIPTION OF THE PREFERRED EMBODIMENTS

Figure 1:
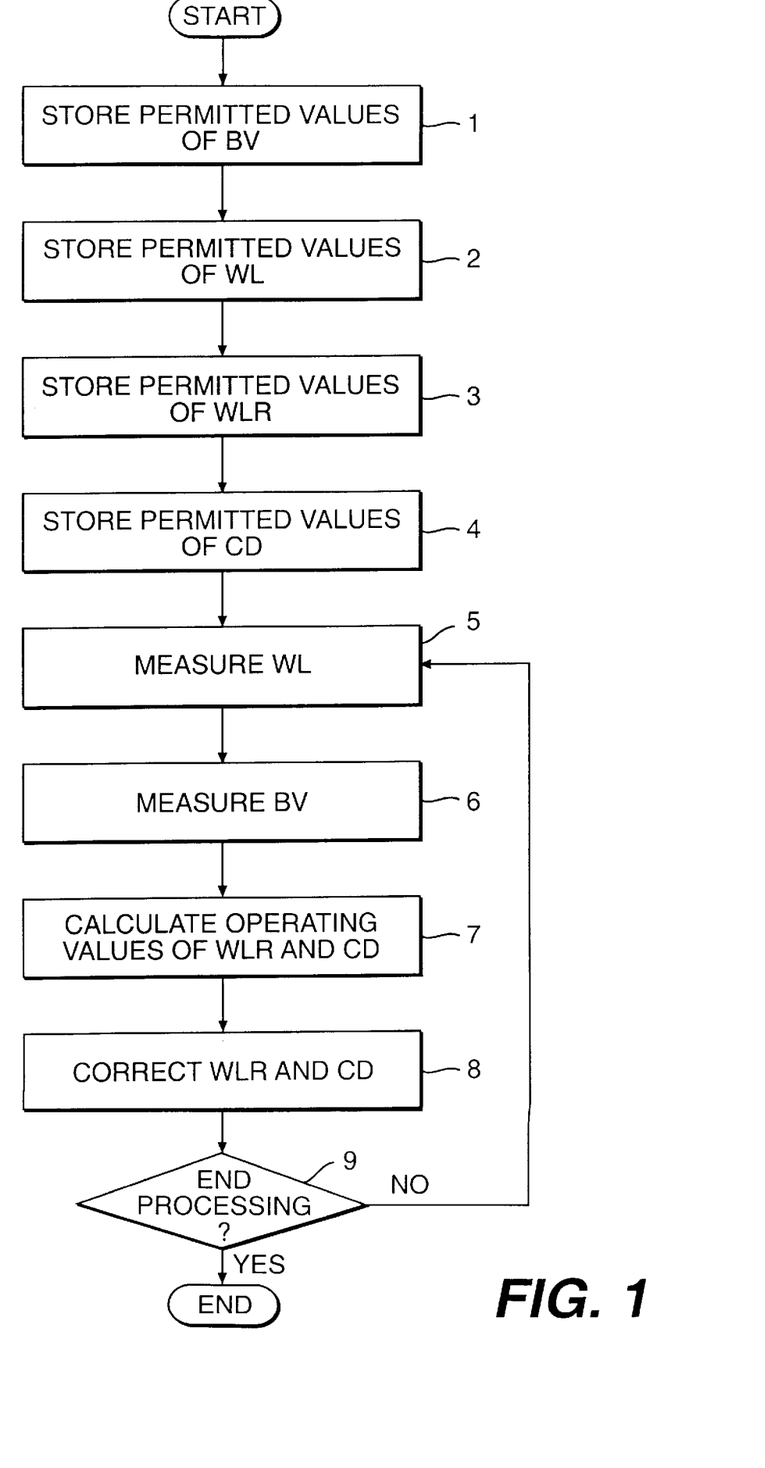
FIG. 1 presents a flow chart relating to the general algorithm used in the dialysis method forming the subject of the invention.

FIG. 1 illustrates a block diagram which shows the phases relating to a dialysis session. In detail, the session starts with the storage of the permitted variation intervals for the few controlled variables during the treatment, with the minimum permitted value and the maximum permitted value. In particular, the permitted variation intervals are stored for the reduction in the blood volume BV (item 1), for the weight loss WL (item 2), for the weight loss rate WLR (item 3) and for the conductivity CD of the dialysis fluid (item 4). The dialysis treatment proper is then started, and the measurements of WL (item 5) and BV (item 6) are taken. With these patient parameters having been noted, the appropriate values of WLR and CD are calculated (item 7), and they are used to correct the previous values of CD and the weight loss rate (item 8). The steps between item 5 and item 8 are repeated so that the treatment is not terminated (as checked using item 9).

Figure 2:
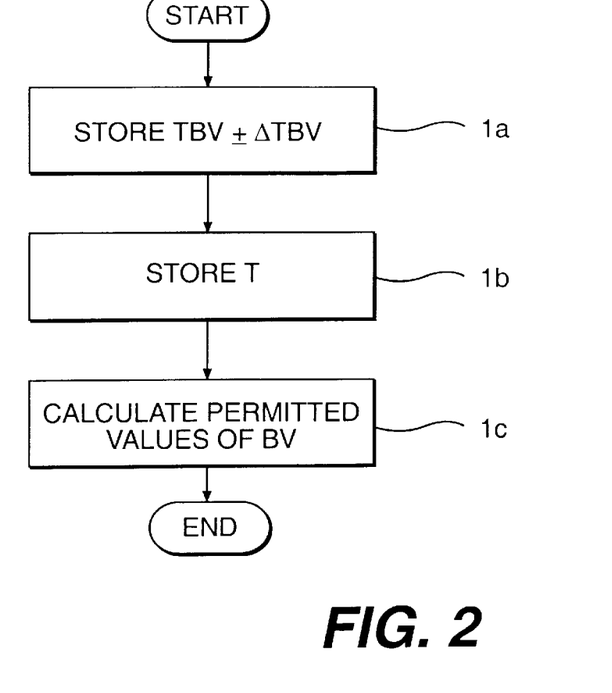
FIGS. 2 and 3 present two detailed flow charts relating to the flow chart in FIG. 1.
Figure 3:
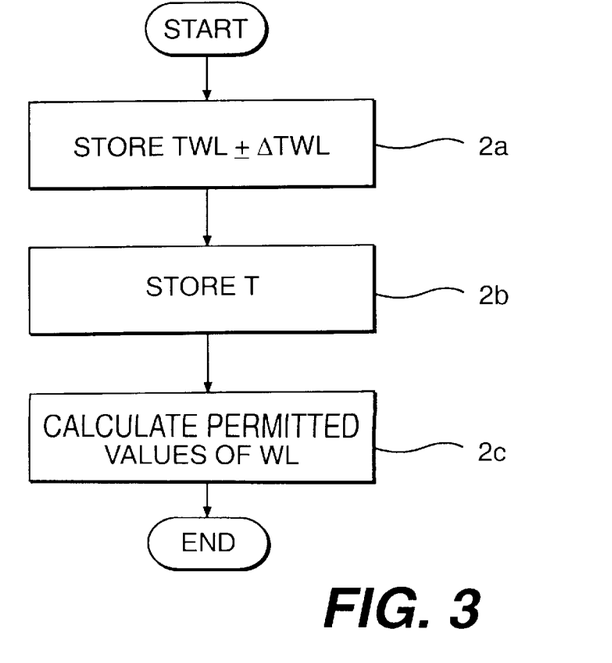

In turn, the phases represented by items 1 and 2 comprise the subroutines represented in FIG. 2 and FIG. 3 respectively. In fact, as shown in FIG. 2, storage of the permitted variation interval of BV (item 1) comprises the storage of the value of BV desired at the end of the treatment (TBV) and the relative tolerances (±ΔTBV) (item 1a), the storage of the treatment duration (T) (item 1b) and the calculation of the extrema of the variation interval of BV permitted during the treatment (item 1c) according to a precise mathematical model or according to valid changes for all the patients, derived from the clinical data analysis.

In contrast, the storage of WL (item 2) comprises (FIG. 3) the storage of the value of WL desired at the end of the treatment (TWL) and the relative tolerances (±ΔTWL) (item 2a), the storage of the treatment duration (T) and the relative tolerances (±ΔT) (item 2b) and the calculation of the extrema of the variation interval of WL permitted during the treatment (item 2) according to a precise mathematical model or according to valid changes for all the patients, derived from the clinical data analysis.

Figure 4:
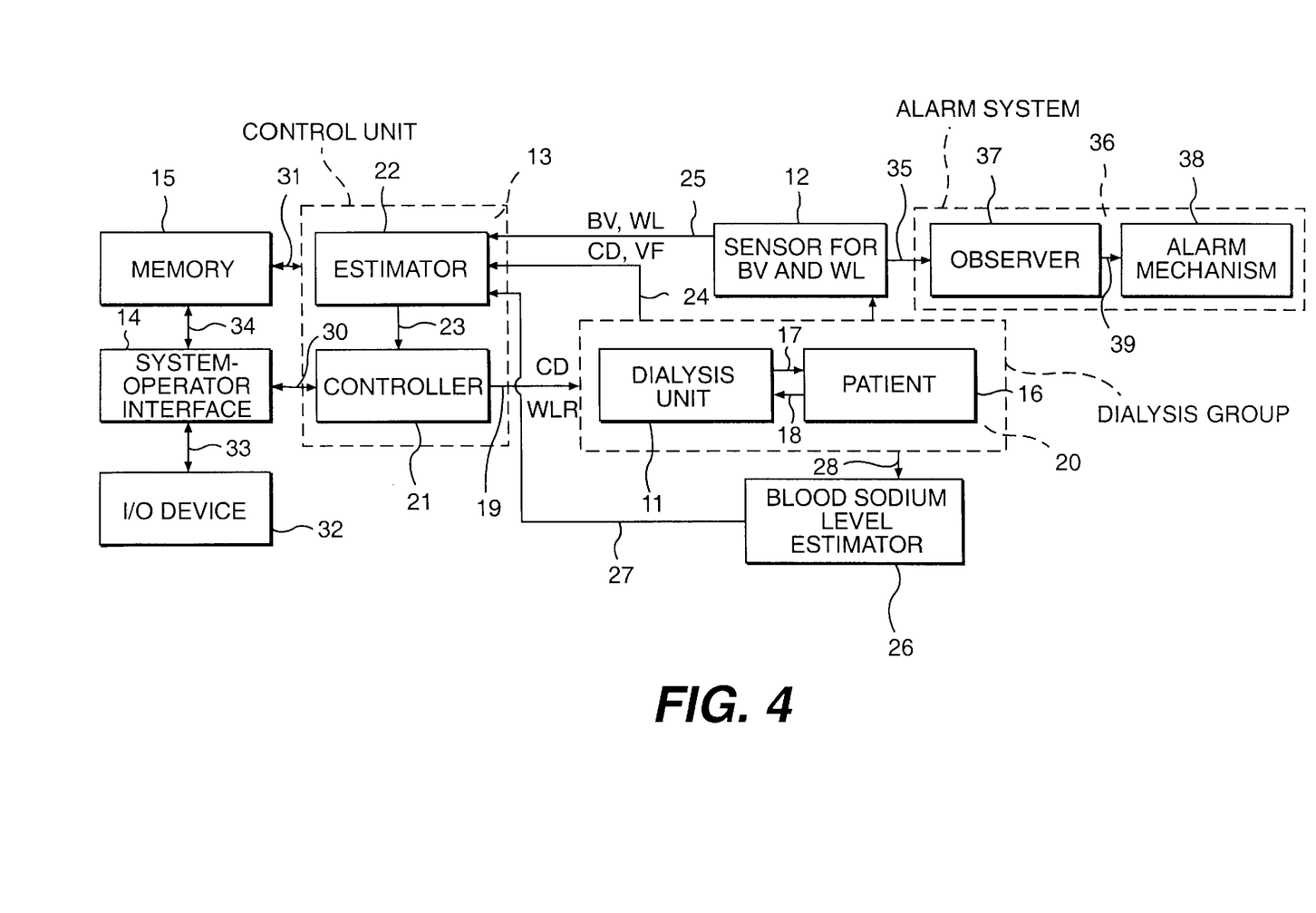
FIG. 4 presents a block diagram of the apparatus forming the subject of the invention.

The automatic dialysis method described above is carried out by the apparatus 10 whose block diagram is illustrated in FIG. 4. The apparatus 10 comprises a dialysis unit 11 which receives two machine parameters (WLR and CD) as prior information, a group of sensors 12 for measuring two actual patient parameters (BV and WL) which are to be controlled, a control unit 13 of the adaptive type which, operating on the machine parameters WLR and CD which it delivers to the dialysis unit 11 and on the actual patient parameters BV and WL measured by the group of sensors 12, makes the patient parameters BV and WL take on the desired changes. These changes are fixed beforehand by an operator using input/output devices 32 which interact with a memory 15 via an apparatus/operator interface 14. In known fashion, the dialysis unit 11, which is of conventional type, is connected to the vascular system of the patient, indicated schematically in FIG. 4 by item 16, using a pair of lines 17, 18, respectively leaving the dialysis unit 11 and entering it, which are connected to a filter through which the patient's blood is passed. From the point of view of the adaptive control performed using the control unit 13, the dialysis unit 11 and the patient 16 form a dialysis group 20 whose link with the group of sensors 12 is schematically represented by an arrow.

In detail, the control unit 13 is connected to the dialysis unit 11 by means of a line 19 which comprises a controller 21 and an estimator 22 communicating with the controller 21 by means of the line 23; the controller 21 and the estimator 22 together define an adaptive controller and are represented separately solely by way of illustration, but in general are embodied by a single component. At its input, the estimator 22 receives signals coming from the dialysis group 20 via the line 24, from the group of sensors 21 via a line 25 and from a blood sodium level estimator 26 via a line 27. The blood sodium level estimator 26 is furthermore connected to the dialysis group 20 via the line 28.

The control unit 13 is furthermore connected via an electrical line 30 to the interface 14 for reading the desired values of the patient parameters BV and WL, of WLR, of CD, of TWL ±ΔTWL, of TVB ±ΔTBV and of T. The control unit 13 furthermore communicates, via a line 31, with the memory 15 in order to exchange the data required to update it, and the results of the updates themselves. The two lines 30, 31 are represented separately merely for the sake of illustration, but they may be formed by a single connection.

The interface 14 is connected to the input/output device 32 through a line 33, and to the memory 15 via a line 34.

Finally, the group of sensors 12 communicates via a line 35 with an alarm system 36 comprising an observer 37 capable of detecting that it has become impossible for the control unit 13 to fulfil its function of keeping the controlled variables BV and WL between the limits of stabilized oscillation, and an alarm mechanism 38 which is connected to the observer 37 via a line 39 and can warn the operator of this control impossibility.

Each item forming the apparatus 10 of the invention is in turn produced at the circuit level using technical means which are known per se. For example, various known control techniques may be used to obtain the stated result. The technique described below represents one of the possibilities chosen, and is presented by way of example, but without limiting the general nature of the solutions which may be applied.

The control unit 13 is based on evaluating an error function which is kept at a minimum value during the dialysis. In the embodiment given, the error function is the linear combination of the intervals of the patient parameters from one time to another, measured from the centres of the allowed intervals; in this linear combination, value weightings inversely proportional to the amplitude of the intervals themselves are used. In particular, the error function considered is:

$$\mathrm{err}(BV(t),WL(t)) = K_{BV} \cdot \mathrm{err}_{BV} + K_{WL} \cdot \mathrm{err}_{WL}$$

where:

$$err_{BV} = BV(t) - \frac{BV_{\min}(t) + BV_{\max}(t)}{2}$$

$$err_{WL} = WL(t) - \frac{WL_{\min}(t) + WL_{\max}(t)}{2}$$

$$K_{BV} = (BV_{\min}(t) - BV_{\max}(t))^{-1}$$

$$K_{WL} = (WL_{\min}(t) - WL_{\max}(t))^{-1}$$

where $K_{BV}$ and $K_{WL}$ are normalization factors (which are a function of the relative importance for obtaining each of the two final objectives established implicitly by the doctor by defining the allowed values).

Other error functions are possible, with the same aim of keeping the control variables within the interval of the allowed values. It is also possible to use different error functions for each of the machine values WLR and CD which, from the point of view of the control, represent two implementation branches.

On the basis of the result of the error function (the function relating to each quantity), the current values of WLR and CD are modified using a regulator of conventional type. In the embodiment given, use is made of a numerical control algorithm programmed on a computer, or the like, within the limitations of continuous systems, and a correction on the forward branch with a stabilizing network, the transfer function of which, in Laplace transform space, has a transfer of gain HO, two poles $p_1$, $p_2$ and two zeroes $z_1$, $z_2$. The poles and zeros, as well as the gain, determine the dynamic behaviour of the control system, and their choice determines the stability of the control and the speed and accuracy in obtaining the result.

The appropriate values of the parameters of the corrector network of each implementation branch (WLR and CD) could be stabilized a priori using conventional control techniques based on evaluating the dynamic response of the patient parameter BV(t) under actual dialysis conditions, using the formulation of mathematical models equivalent to the patient according to the read data. However, this approach is often inadequate because it presupposes a constant individual reaction to WLR and to CD, considered as the triggers capable of modifying the BV (besides the WL), whereas in reality this reaction can vary from one individual to another and for the same individual at different times.

With the aim of adapting the inherent behaviour to the individual variations of the patients, the controller which is implemented therefore uses a module, represented by the estimator 22, which makes it possible to identify the different responses of the patient to the stresses imposed by the dialysis apparatus, with periodic estimation of the parameters of the dialysis-unit/patient model which are linked with the sensitivity of the BV to the variations in WLR and CD. The availability of the dialysis-unit/patient model, identified at time t, makes it possible to use an optimum control technique to calculate the parameters of the correction network described (WLR and CD) or to synthesize the most appropriate correction network to achieve the minimum value of the error function in the shortest possible time and with a sufficient stability margin.

In contrast, as regards the initial input of the desired parameters, a possible simplified embodiment of the method for programming the tolerance limit values as a function of time is then represented as stated in more detail below, by inputting the limit values at the end of dialysis $BV_{min}(t_{fin})$, $BV_{max}(t_{fin})$, $WL_{min}(t_{fin})$, $WL_{max}(t_{fin})$, while the morphology of the curve joining these final points to the initial values $BV_{min}(O)$, $BV_{max}(O)$, $WL_{min}(O)$, $WL_{max}(O)$ (by definition zero, so long as there is no variation in the blood volume or weight loss at the start of the treatment) is derived from experience and programmed in the form of a normalized mean curve valid for all the patients, or a mathematical interpolation law defined a priori, or alternatively a mathematical model which integrally describes the fluid transfers which take place in the patient as a function of the weight loss and the diffusion exchanges through the dialysis membrane.

Figure 6:
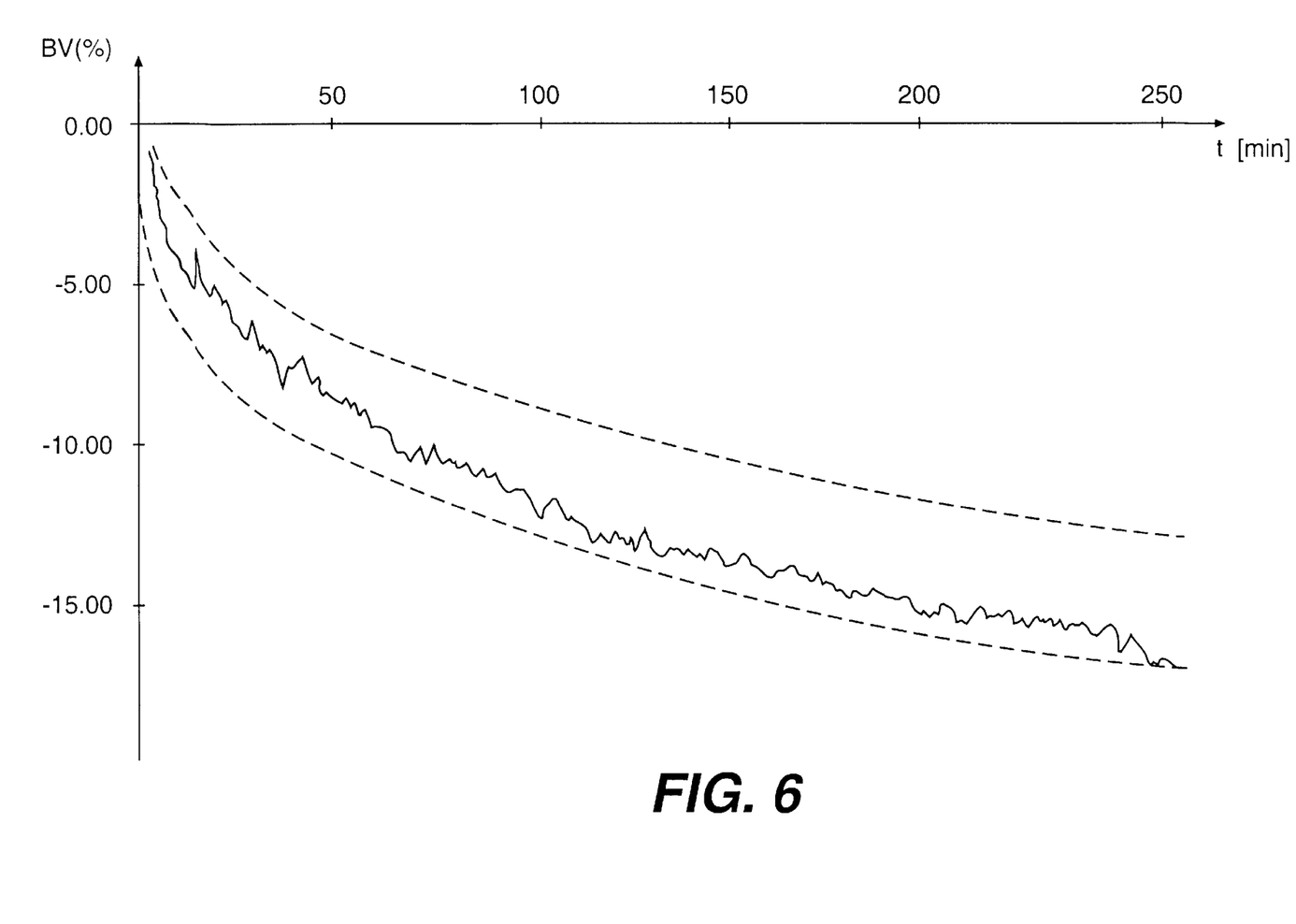
Figure 7:
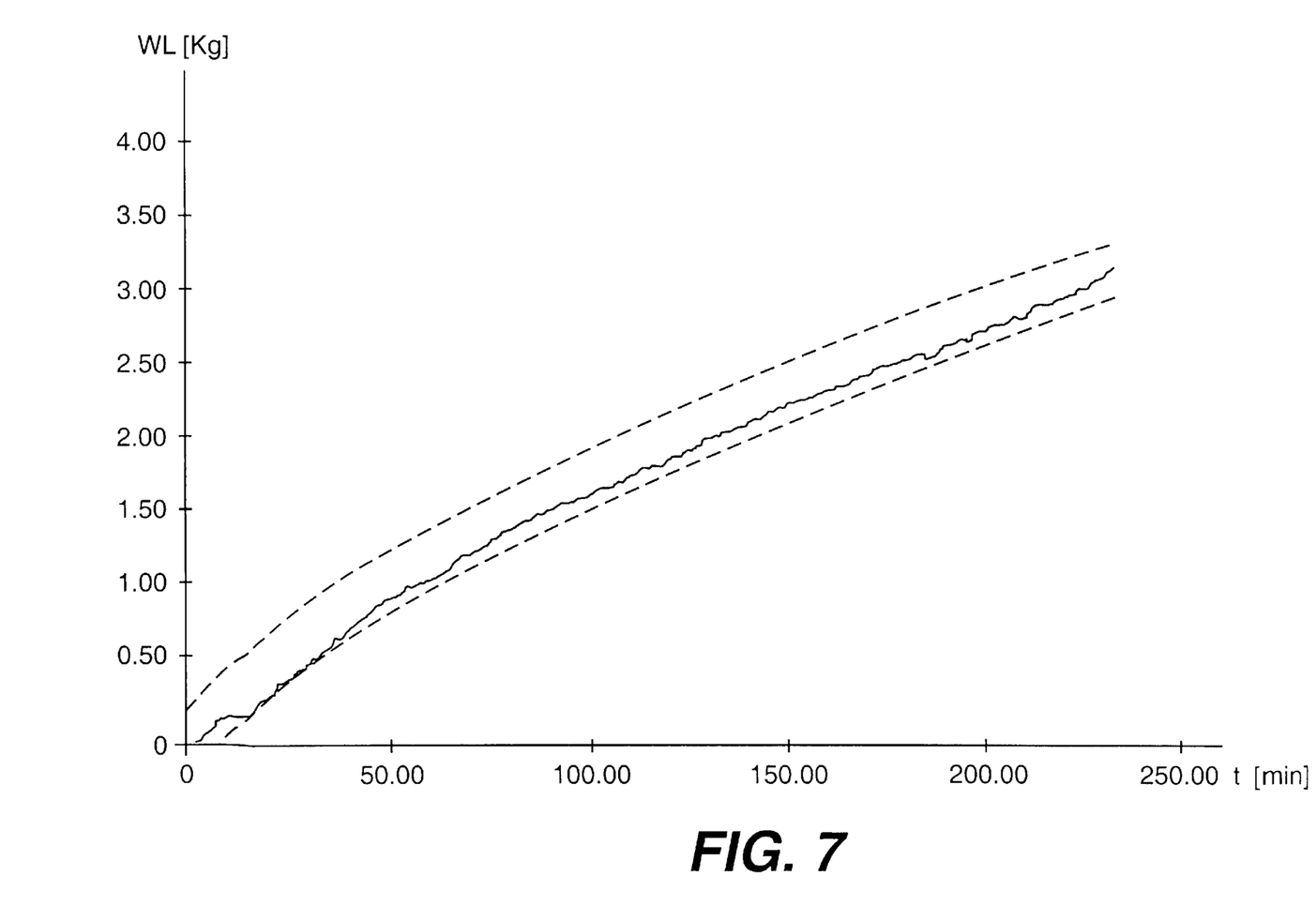

In trials carried out by the Applicant Company, use was made of empirical curves obtained using the response to the treatment of a population of patients who did not exhibit intradialysis symptomatology. Specifically, FIG. 6 illustrates the change in the variation of the blood volume during the treatment (continuous line) and the relative permitted variation margins (broken lines), while FIG. 7 illustrates the change in the total weight loss during the treatment (continuous line) and the relative permitted variation margins (broken line). It should further be recalled that the value of the total weight loss is equal to the integral of the weight loss rate.

The allocated margin variability for obtaining the objectives is dependent on the variability of the population of haemodialyzed patients, which includes individuals who are particularly sensitive to the variations in blood volume and are consequently subject to intradialysis pathologies relating to the cardiovascular system, while there are patients who have greater tolerance but who nevertheless need rigorous bodyweight control.

In contrast, as regards the observer 37 of the tendency of the controlled variables in terms of situations of exceeding the set limits, it has the purpose of predicting a future excess and of warning the operator of this early enough for him to be able to implement corrective operations, such as those described above, in good time. The implementation techniques may, for example, be based on measuring the time derivatives of the differences $BV(t)-BV_{min}(t)$, $BV(t)-BV_{max}(t)$, $WL(t)-WL_{min}(t)$, $WL(t)-WL_{max}(t)$.

The blood sodium level estimator 26 is, in contrast, based on calculating the patient blood sodium level Na(t) by integrating the effect of CD in a dialysis-unit/patient model on the basis of a measured or assumed value of the initial sodium concentration in the patient's plasma. According to a first solution, it is possible to employ a simple single-compartment representation of the sodium distribution volume in the patient, in which the exchanges are represented by diffusion and convection through the dialysis membrane.

It is also possible to employ means for measuring the plasma ionic concentration, which means directly or indirectly measure Na(t) and thus make it possible to avoid having to employ imprecise mathematical models. By having information regarding the change in the patient's plasma sodium level, it is then possible to take it into account in the function which drives the CD actuation device. For example, the previous error function may become:

$$\mathrm{err}(BV(t),WL(t)) = K_{BV1} \cdot \mathrm{err}_{BV} + K_{WL} \cdot \mathrm{err}_{WL} + K_{Na} \cdot \mathrm{err}_{Na}$$

in which the terms in common with the previous error function take the same values and expressions, while:

$$err_{NA} = Na(t) - \frac{Na_{\min}(t) + Na_{\max}(t)}{2}$$
$$K_{Na} = (Na_{\min}(t) - Na_{\max}(t))^{-1}$$

with a normalization factor $K_3$ similar to the previous one.

The operation of the automatic dialysis apparatus 10 is described with reference to the flow charts in FIGS. 1–3.

To obtain the control result, the apparatus 10 checks at time t that the measured values of BV and WL belong to the allowed value intervals and can produce WLR and CD at each instant between the allowable value intervals, in order to keep them simultaneously away from the allowed variability limits for the controlled variables WL and BV.

In particular, the dialysis treatment starts by the operator inputting variation intervals permitted during the treatment (item 1) for BV, WL, WLR and CD, as well as the duration T of the treatment. These values are input using I/O devices 32 and are successively managed by the interface 14 which stores them in the memory 15 and sends them to the control unit 13. The control unit 13 then controls the dialysis group 20 on the basis of the initial machine parameters WLR and CD, and thus starts the session proper. The group of sensors 12 detects the first samples of the patient parameters BV and WL (items 5, 6) and sends them, with the machine parameters CD, WLR and the blood sodium level calculated by the blood sodium level estimator 26, to the estimator 22 of the parameters of the dialysis-unit/patient model. The estimator 22 thus calculates the control coefficient values 21 which link the actual WLR and CD to the errors relating to BV and WL and (item 7) communicates them to the controller 21 which corrects the machine parameters CD and WLR sent to the dialysis group 20 (item 8).

The observer 37 detects the variations in the patient parameters BV and WL and communicates to the alarm mechanism 38 a possible tendency of the parameters BV and WL to exceed the permitted intervals, so that the operator can decide to continue the automatic dialysis or alter the allowed variation limits. If this were not possible, the operator could also decide to interrupt the automatic treatment and manually terminate the session.

Figure 5:
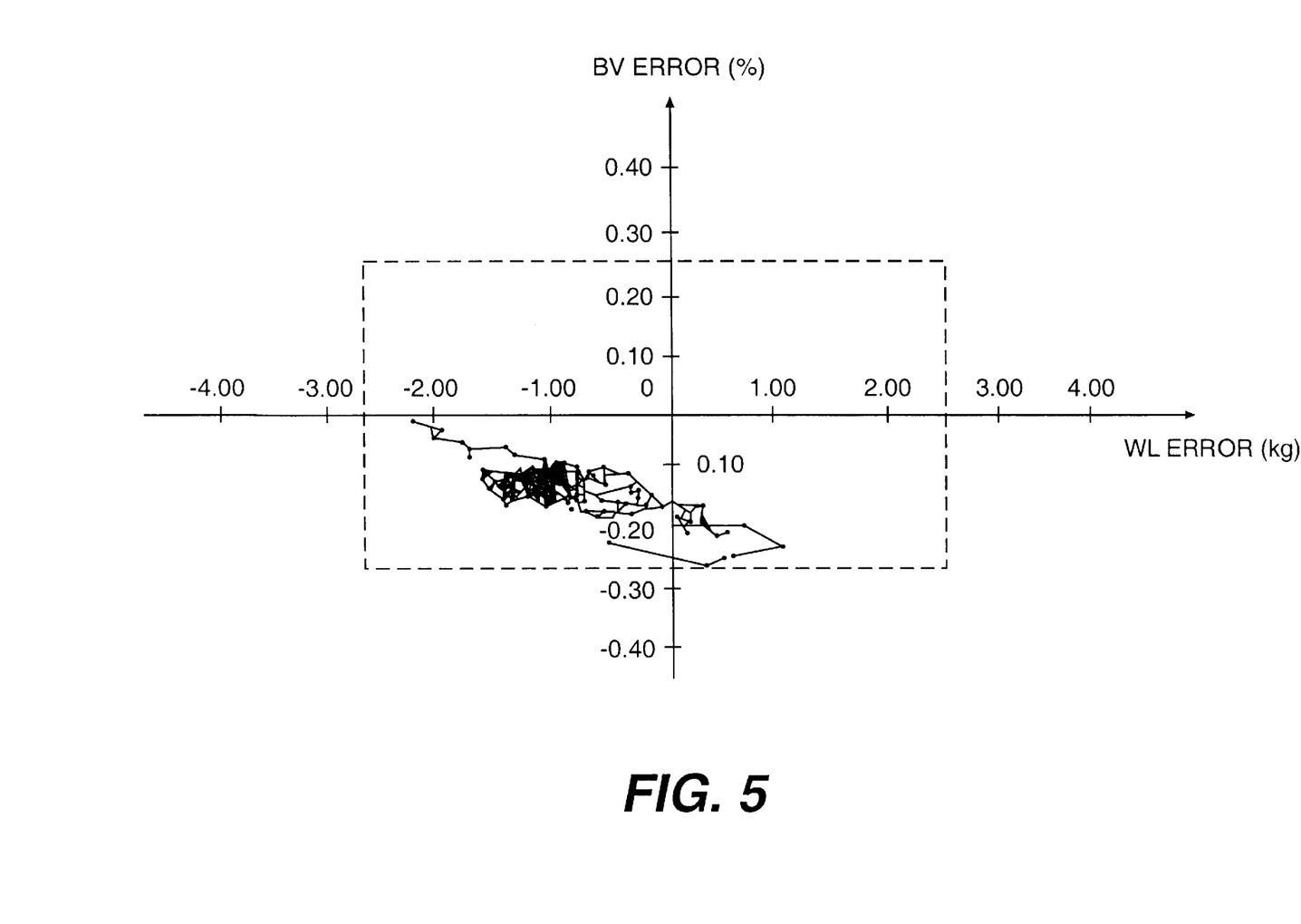
FIGS. 5 to 7 show diagrams relating to the change in the variables used in the method of the invention.

In addition to inputting the data which the apparatus requires to operate correctly, the I/O devices 32 also allow synthetic representation (FIG. 5) of the simultaneous positioning of the patient parameters relative to the current allowability intervals, so that the person in charge of the dialysis treatment can straight away establish the proper running of the automatic dialysis treatment and the use of the allowed variation margins.

The machine and patient parameter acquisition cycle and the calculation of the new machine parameters continue until the time T, set as the duration of the session, has elapsed.

Finally, it is clear that modifications and variants may be added to the method and the apparatus described and represented here, without thereby departing from the scope of the invention. For example, it is possible to produce an apparatus without a blood sodium level estimator or alarm mechanism without thereby altering its functions.

We claim:

1. Method for automatic dialysis using a dialysis unit which, in service, is connected to a patient undergoing a dialysis treatment, comprising the phases of acquiring allowed values of input parameters and desired values of patient parameters, acquiring actual values of the patient parameters; acquiring actual values of machine parameters; and controlling the operation of the dialysis unit using controlled values of the machine parameters to make the patient parameters take on the desired values, wherein:

the patient parameters comprise the relative variation in blood volume (BV) and the weight loss (WL), the machine parameters comprise the weight loss rate (WLR) and the conductivity of the (CD) dialysis fluid, the phase of acquiring allowed values of the input parameters and desired values of the patient parameters comprises the phases of:

storing the permitted values of the relative variation in blood volume as a function of the dialysis time;

storing the permitted values of the weight loss as a function of the dialysis time;

storing the permitted values of the weight loss rate as a function of the dialysis time;

storing the permitted values of the conductivity of the dialysis fluid as a function of the dialysis time;

the phase of acquiring the actual values of the patient parameters comprises the phases of:

acquiring actual values of the weight loss during the treatment;

acquiring actual values of the variation in blood volume during the treatment;

the phase of controlling the operation of the dialysis unit comprises the phases of:

calculating the operating values of the weight loss rate and of the conductivity of the dialysis fluid; and correcting the weight loss rate and the conductivity of the dialysis fluid on the basis of the operating values.

2. Method according to claim 1, wherein the calculation phase comprises calculating the values of the weight loss rate and of the conductivity of the dialysis fluid, so that the weight loss rate, the dialysis fluid conductivity, the relative variation in the blood volume and the weight loss remain within respective permitted values.

3. Method according to claim 1 or 2, wherein the phase of storing the permitted values of the relative variations in blood volume comprises the phase of:

storing a desired value of the variation in the blood volume at the end of the treatment as well as the permitted relative tolerances;

storing a treatment duration;

calculating and storing the permitted values of the relative variation in blood volume, as a function of the dialysis time, according to a mathematical model or according to clinical data analysis.

4. Method according to claim 1, wherein the phase of storing the permitted weight loss values comprises the phases of:

storing a desired value for weight loss at the end of the treatment as well as permitted relative tolerances;

storing a treatment duration;

calculating and storing the permitted values of weight loss as a function of the dialysis time, according to a mathematical blood model or according to clinical data analysis.

5. Method according to claim 1, wherein the calculation phase comprises the phase of determining the values of the weight loss rate and of the conductivity of the dialysis fluid on the basis of a mathematical blood model having at least the actual patient parameters as input and the weight loss rate and the conductivity of the dialysis fluid as output.

6. Method according to claim 5, wherein
the calculation phase comprises an optimization phase using the estimation of the coefficients of the model on the basis of an evaluation of the variation in blood volume as a function of the weight loss rate and of the conductivity of the dialysis fluid.

7. Method according to claim 1, wherein
the calculation phase comprises a phase of reducing an error function between the desired patient parameters and the actual patient parameters.

8. Method according to claim 1, wherein
the phase of acquiring the allowed values of the input parameters and the desired values of the patient parameters comprises the phase of acquiring a value of the patient's blood sodium level.

9. Method according to claim 1, wherein
the method comprises a phase of synthetic representation of the simultaneous position of the actual values of the patient variables and of the respective tolerances.

10. Method according to claim 1, wherein
it comprises an alarm signal generation phase in the event that the actual patient variables tend to depart from the respective permitted value intervals.

11. Method according to claim 10, the alarm signal generation phase comprises the phase of calculating time derivatives of the differences between the actual values and the permitted values of the variation in blood volume and between the actual values and the permitted values of the weight loss.

12. Automatic dialysis apparatus, comprising a dialysis unit, means for acquiring allowed values of input parameters and desired values of patient parameters; means for acquiring the actual values of the patient parameters; means for acquiring the actual values of the machine parameters; and means for controlling the operation of the dialysis unit using operating values of the machine parameters in order to make the patient parameters take on the desired values; wherein:
the patient parameters comprise the relative variation in blood volume (BV) and the weight loss (WL),
the machine parameters comprise the weight loss ratio (WLR) and the conductivity of the (CD) dialysis fluid,
the acquisition means comprise:
means for storing the permitted values of the relative variation in blood volume as a function of the dialysis time;
means for storing the permitted values of the weight loss as a function of the dialysis time;
means for storing the permitted values of the weight loss rate as a function of the dialysis time;
means for storing the permitted values of the conductivity of the dialysis fluid as a function of the dialysis time;
the means for acquiring the actual values of the patient parameters comprise:
means for acquiring the actual values of the weight loss, at each instant during the treatment;
means for acquiring the actual values of the variation in blood volume, at each instant during the treatment;
the means for controlling the operation of the dialysis unit comprise:
means for calculating the operating values of the weight loss rate and of the conductivity of the dialysis fluid;
means for correcting the values of the weight loss rate and of the conductivity of the dialysis fluid, on the basis of the operating values.

13. Apparatus according to claim 12, wherein
the means for acquiring the allowed values of the input parameters and the desired values of the patient parameters comprise a device for inputting and displaying data, an apparatus/operator interface device and memory devices.

14. Apparatus according to claim 12 or 13, wherein
the means for acquiring the actual values of the patient parameters comprise sensors.

15. Apparatus according to claim 12, wherein
the control means comprise a controller and an estimator of the weight loss rate and the conductivity of the dialysis fluid according to a mathematical blood model having at least the actual patient parameters as input and the weight loss rate and the conductivity of the dialysis fluid as output.

16. Apparatus according to claim 15, wherein
the estimator comprises means for optimizing the weight loss rate and the conductivity of the dialysis fluid, the optimization means being capable of estimating the coefficients of the model on the basis of an evaluation of the variation in the blood volume as a function of the weight loss rate and of the conductivity of the dialysis fluid.

17. Apparatus according to claim 12, comprising means for estimating the patient's blood sodium level.

18. Apparatus according to claim 15, wherein
the estimator comprises means for optimizing the weight loss rate and the conductivity of the dialysis fluid, which can estimate the coefficients of the model on the basis of an evaluation of the variation in the blood volume as a function of the weight loss rate, of the conductivity of the dialysis fluid and of the blood sodium level.

19. Apparatus according to claim 12, comprising means for detecting a deviation, capable of detecting a possible deviation of the actual patient parameters outside the permitted value intervals.

20. Apparatus according to claim 19, wherein
the means for detecting the deviation comprise means for observing the deviation and means for signalling the deviation, and in that the observer comprises means for calculating the time derivatives of the differences between the actual values and the permitted values of the variation in the blood volume and between the actual values and the permitted values of the weight loss.

21. Apparatus according to claim 13, characterized in that the device for inputting and displaying data comprises means for synthetic representation of simultaneous positions of the patient variables and of the permitted value intervals.

* * * * *

UNITED STATES PATENT AND TRADEMARK OFFICE
CERTIFICATE OF CORRECTION

PATENT NO. : 5,938,938
DATED : August 17, 1999
INVENTOR(S) : Bosetto, et al.

It is certified that error appears in the above-identified patent and that said Letters Patent is hereby corrected as shown below:

Claim 11, col. 9, line 25, before "the alarm signal," insert -- wherein --.

Signed and Sealed this

Sixth Day of March, 2001

Attest:

NICHOLAS P. GODICI

Attesting Officer     Acting Director of the United States Patent and Trademark Office